United States Patent [19]

Devins et al.

[11] Patent Number: 4,522,065
[45] Date of Patent: Jun. 11, 1985

[54] REMOTE PRESSURE SENSOR

[75] Inventors: John C. Devins, Burnt Hills; Amandus H. Sharbaugh, Clifton Park, both of N.Y.

[73] Assignee: General Electric Company, Schenectady, N.Y.

[21] Appl. No.: 595,780

[22] Filed: Apr. 2, 1984

[51] Int. Cl.³ .............................................. G01L 9/00
[52] U.S. Cl. .................................... 73/705; 250/231 P
[58] Field of Search ................ 73/705, 30; 250/231 P, 250/231 R

[56] References Cited

U.S. PATENT DOCUMENTS 3,398,582  8/1968  McFarland ........................... 73/705
4,147,431  3/1979  Mann ................................... 73/705

Primary Examiner—Donald O. Woodiel
Attorney, Agent, or Firm—Bernard J. Lacomis; James C. Davis, Jr.

[57] ABSTRACT

The pressure of a gas within an enclosure is measured without making physical contact with the gas by focusing radiation from a laser onto a section of the gas and, while varying the intensity of the radiation, monitoring the section under measurement for electrical breakdown, as indicated by emitted light or suitable breakdown indicia, such as radio noise. The absolute gas pressure at the section of the gas under measurement is determined from a calibration curve relating the intensity of the beam to the pressure at which breakdown occurs for the particular gas being monitored.

7 Claims, 1 Drawing Figure

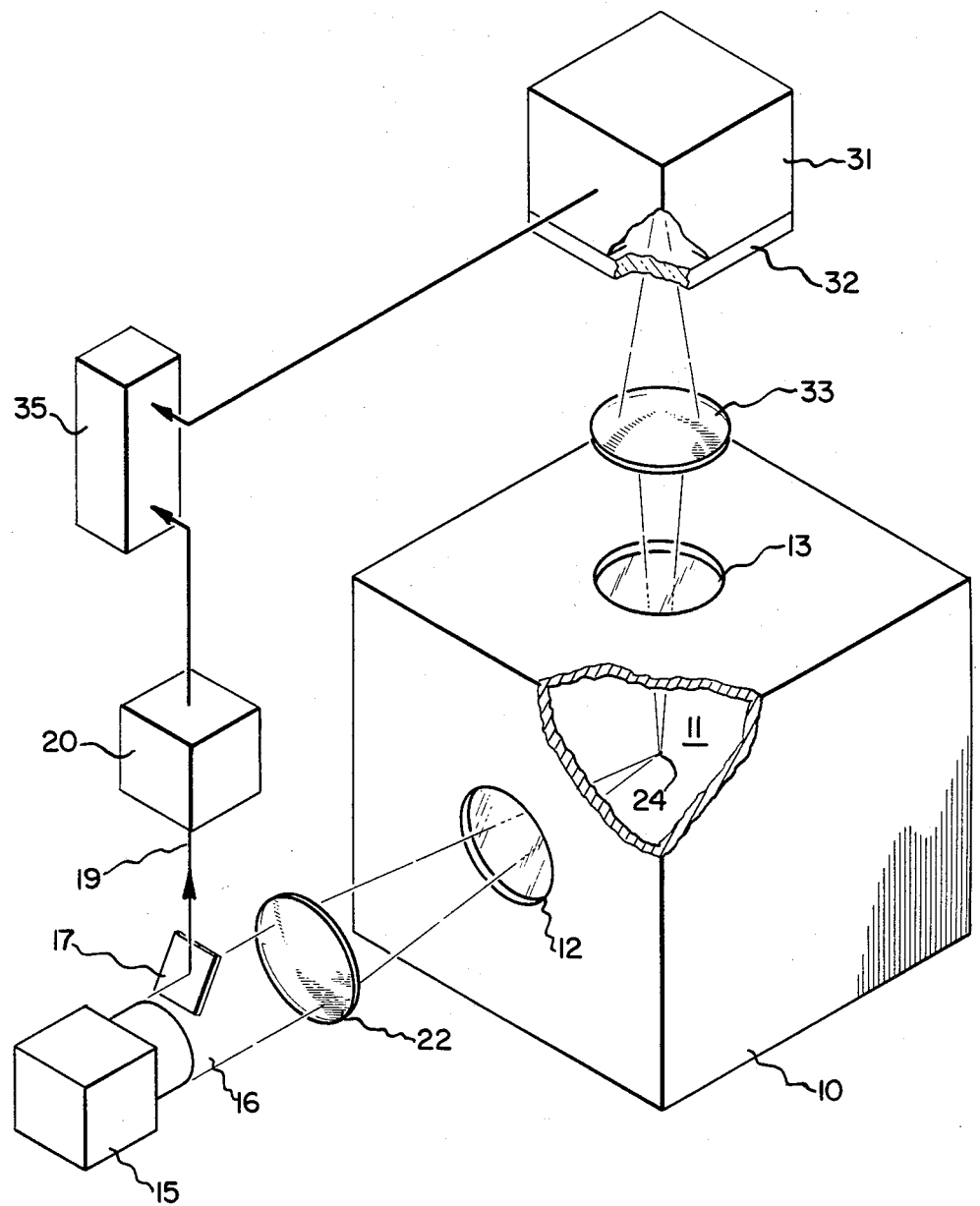

REMOTE PRESSURE SENSOR

BACKGROUND OF THE INVENTION

The present invention relates to methods and apparatus for measuring the pressure of a gas without physical contact with said gas. More particularly, the present invention relates to a system of the above general type which permits the measurement of the pressure of a gas at a preselected small volume or point within a larger volume of the gas. Specifically, the invention relates to a sensing apparatus and method for measuring the pressure of a gas or vapor by focusing radiation on a small section of the gas, varying the intensity of said focused radiation from below an intensity level at which electrical breakdown occurs to a level at which breakdown occurs and monitoring the gas under test to detect electrical breakdown and the light intensity level at which such electrical breakdown occurs. The light intensity level at breakdown is then used to determine pressure of the gas by consulting a reference or characteristic curve for the gas or vapor under test which relates the intensity of radiation to pressure at breakdown. Such a characteristic curve could be developed by means of a separate experiment for the particular gas under test.

In many industrial processes it is desirable to know the local pressure of a gas at points within a reaction chamber in order to control or optimize the reactions or processes taking place within such chamber. It is important in many such processes to be able to measure the pressure of a gas without any physical intrusion into the environment which contains the gas so as to avoid any interference with the reaction process.

Generally, non-contacting pressure sensors are desirable in situations where information on the pressure of a gas is desired but contact with a gas is impractical for various reasons. Such a situation exists where the pressure of a gas at a specific reaction section in a chamber is desired and the gas exhibits a large pressure gradient across the larger volume of the reaction enclosure. In such a situation it is not practical, if not impossible, to rapidly locate and change the position of a sensor in the enclosure confining the gas. Moreover, the volume of the gas under study may be too small to use conventional techniques.

To overcome these and other problems, non-contacting sensors for measuring various properties of a gas have been developed. Several techniques are known which involve the projection of a beam of light toward a moving gas stream, detecting components of the beam reflected, scattered, or otherwise modified by the moving gas, and analyzing the effect of the motion upon the detected beam either independently of or in comparison with the transmitted beam. The above techniques are known to involve use of a laser for the projected beam and optical detection techniques for analyzing the frequency, intensity, or other changes in the beam brought about by the moving gas.

OBJECTS OF THE INVENTION

Accordingly, a principal object of the invention is the provision of a non-contacting gas pressure measurement technique and apparatus.

A further object is the provision of a non-contacting gas pressure measurement technique and apparatus capable of determining the pressure of a gas at a specific small area within a large container of such gas.

A still further object is the provision of such a technique and apparatus which operates to provide a gas pressure measurement at a preselected small area within a larger gaseous region which is subject to large pressure gradients.

A further object is to provide such a system which is relatively inexpensive to construct and reliable in operation.

Further objects and advantages of the present invention will become apparent from a reading of this specification in conjunction with the included drawings.

SUMMARY OF THE INVENTION

The above noted and other objects of the invention are accomplished by a method and apparatus for measuring the pressure of a gas or vapor within a closed chamber without making physical contact with the gas by focusing radiation emitted by a laser or other suitable radiation source onto a section of the gas. The intensity of the radiation is increased from below the level at which electrical breakdown of the gas occurs to the level at which breakdown is detected (as indicated by emitted light or radiofrequency noise) while means are provided to correlate the gas breakdown point with the intensity level of the radiation at breakdown. The absolute gas or vapor pressure at the location of the gas under measurement is determined (either by hand or via an instrument) from a calibration curve relating the intensity of the radiation at breakdown to the pressure of the gas under test.

BRIEF DESCRIPTION OF THE DRAWING

The subject matter which is regarded as the invention is particularly pointed out and distinctly claimed in the concluding portion of the specification. The invention, however, both as to organization and method of practice, together with further objects and advantages thereof, may best be understood by reference to the following description taken in connection with the accompanying drawing which shows an illustrative arrangement for carrying out the apparatus and method of the invention.

DETAILED DESCRIPTION OF THE INVENTION

As is mentioned hereinbefore, a need exists for accurate, sensitive, non-contacting sensors to measure the pressure of a gas in a reaction area to optimally control the reaction process. Similar needs arise in other applications wherein it is desirable to measure the pressure of a gas under conditions which do not afford the opportunity of physical intrusion into the gas container or enclosure for various reasons. It is particularly important in some of the above situations to be able to monitor pressure at a given small point within a large volume of gas, such as the point or small area at which a reaction is taking place or being initiated. This is a particularly desirable feature in situations where, due to turbulence of the component gases, large pressure gradients exist and the average pressure or the pressure at a point remote from the reaction site would be substantially different than the one measured at the reaction site.

A generalized description of the system of the present invention as employed for the measurement of pressure at a selected point within a larger volume of gas may be explained with reference to the drawing in which a container 10 is shown which in its interior space 11 encloses a gas to be monitored or measured according to the present invention. The enclosure 10 is provided with monitoring ports 12 and 13 consisting of openings in which suitable transparent, but gas impervious, barriers are mounted by any appropriate means.

A source of radiant energy as, for example, a laser 15 emits a main beam 16 of collimated light which is incident upon a partially transmissive, partially reflecting beam splitter 17 which provides a monitoring component beam 19 which is directed at an angle to the main beam 16 and incident upon a photodetector 20. The purpose of the photodetector 20 is to provide an electrical signal which is an indicator of the intensity of the beam 16 at any given moment during the test. Preferably, only a small portion of the main beam is intercepted by the beam splitter 17 to accomplish this purpose in a well known manner.

A focusing lens 22 is situated to intercept and focus the main beam 16 onto a selected point 24 or small area of the volume 11 within the container 10. This is accomplished by directing the focused main beam through the optical entrance port 12.

A light detector 31 is located to monitor light emitted from the point in the enclosure at which the main beam is focused. The detector may be of conventional construction and may include an optional filter 32 to prevent light at the frequency of source 15 from impinging thereon. A lens 33 which operates to focus light emitted from point 24 onto the sensing surface of the photodetector 31 is located in a suitable position juxtaposed to the optically transmissive port 13.

In the preferred embodiment of the invention the source of light 15 may be a Q switched laser of the type having, for example, provisions for variation in the intensity of its output either manually or under the control of a suitable controller in a predictable manner. The laser must provide a sufficient amount of energy to cause breakdown of the gas under test, typically between 0.1–0.5 joule released in a 10–30 nanosecond pulse. Lasers of this type using ruby and carbon dioxide as the lasing medium are commercially available.

In order to determine the pressure of a gas within the enclosure 10, a laboratory experiment is performed to provide a characteristic curve relating the output intensity of the laser 15 to the pressure of the gas at which breakdown takes place. Characteristic curves for typical gases desired to be monitored could be generated for use in the monitoring system of the invention.

To determine the actual pressure of the gas at monitored point 24 within the enclosure, the light would first be focused on the desired area to be monitored with the intensity of the beam chosen to be below the known breakdown point for the gas under test. The optical monitoring device 31 and lens 33 may need to be adjusted to provide a suitable monitoring of the chosen point within the chamber being monitored.

The intensity of the main beam 16 from source 15 is then increased while concurrently being monitored by the photodetector 20, the output of which provides a first input to a control circuit 35. As the intensity of beam 16 is increased the level is reached at which the gas at point 24 is broken down, resulting in a short burst of emitted light therefrom at a frequency different than the source frequency. This burst is detected by the photodetector 31, the output of which is also fed as the other input to the control circuit 35. The control circuit may read out directly the intensity of light at the time breakdown occurred. Alternately, the control circuit 35 may include a microprocessor which is preprogrammed by the provision of look-up tables of characteristic curves in memory so that it reads out directly the pressure of the gas being monitored from the data and inputs supplied and the known composition of the gas within the enclosure.

Although the above described embodiment includes a source of optical radiation, with optical beam directing and detecting devices, it should be apparent that other types of radiation sources may be used with appropriate beam directing and detecting means. It may, for example, be appropriate to use electromagnetic radiation sources of various other frequencies. While the preferred embodiment has been disclosed utilizing an optical detection arrangement to identify electrical breakdown of the gas under test, it is understood that other means which, for example, monitor emitted radiofrequency may be suitable to provide such an indication.

From the above, it is apparent that although the invention has been described hereinbefore with respect to certain specific embodiments and preferred illustrations, it is evident that many modifications and changes may be made without departing from the spirit of the invention. Accordingly, by the appended claims, we intend to cover all such modifications and changes as fall within the true spirit and scope of this invention.

What we claim as our invention and desire to have secured by Letters Patent of the United States is:

1. Apparatus for measuring the pressure of a gas within an enclosure comprising:
   (a) means for generating a beam of light,
   (b) means for focusing said beam at a preselected point within said enclosure,
   (c) means for varying the intensity of said beam to cause electrical breakdown of the gas at a preselected point, and
   (d) detector means for measuring the intensity of said beam at which said electrical breakdown occurs.

2. The combination recited in claim 1 wherein said detector means includes a first photodetector and a beam splitting means in the path of said beam for directing a first component of said beam toward said photodetector.

3. The combination recited in claim 2 wherein said detector means further includes a second photodetector for optically monitoring said point at a frequency different than the frequency of said beam.

4. The combination recited in claim 3 further including means responsive to said electrical signals generated by said first and second photodetectors for providing an output indicative of the pressure of said gas.

5. Apparatus as described in claim 4 wherein said detector means further includes a display for indicating the pressure of gas by correlating the measured intensity of said beam at breakdown with the pressure breakdown characteristics of a given gas being monitored.

6. Apparatus as described in claim 1 or claim 3 wherein means for generating comprises a laser for generating a beam of coherent light.

7. The method of determining the pressure of a gas within an enclosure comprising the steps of:
   (a) focusing a beam of light on a small volume of said gas,
   (b) increasing the intensity of said beam starting from a level below the electrical breakdown point of said gas,
   (c) monitoring said volume to detect electrical breakdown,
   (d) determining the intensity of said beam at which electrical breakdown occurs, and
   (e) correlating the information obtained in (d) with the known characteristics for the gas being monitored to provide an indication of pressure at said volume under test.

* * * * *